(12) United States Patent
Peltier

(10) Patent No.: US 6,280,193 B1
(45) Date of Patent: Aug. 28, 2001

(54) ZIRCONIUM OXIDE DENTAL IMPLANT WITH INTERNAL THREAD

(75) Inventor: Guy Peltier, Rueil-Malmaison (FR)

(73) Assignee: Jeanine Gourlaouen-Preissler (FR); a part interest ( * ) Notice: Subject to any disclaimer, the term of this patent is extended or adjusted under 35 U.S.C. 154(b) by 0 days.

(21) Appl. No.: 09/308,666

(22) PCT Filed: Sep. 30, 1998

(86) PCT No.: PCT/FR98/02094

§ 371 Date: Sep. 13, 1999

§ 102(e) Date: Sep. 13, 1999

(87) PCT Pub. No.: WO99/17675

PCT Pub. Date: Apr. 15, 1999

(51) Int. Cl.[7] ................................................. A61C 8/00
(52) U.S. Cl. ........................................ 433/174; 433/201.1
(58) Field of Search ................................. 433/174, 173, 433/201.1

(56) References Cited

U.S. PATENT DOCUMENTS

| 3,589,011 | * | 6/1971 | Sneer ................................. 433/174 |
| 4,259,072 | * | 3/1981 | Hirabayashi et al. . |
| 4,668,191 | * | 5/1987 | Plischka .............................. 433/174 |
| 4,983,182 | * | 1/1991 | Kijima et al. ..................... 433/201.1 |
| 5,192,325 | * | 3/1993 | Kijima et al. ..................... 433/201.1 |
| 5,397,362 | * | 3/1995 | Noda ................................ 433/201.1 |
| 5,824,089 | * | 10/1998 | Rieger .............................. 433/201.1 |

FOREIGN PATENT DOCUMENTS

08038512 * 7/1994 (JP) .
474571 * 7/1994 (EP) .

* cited by examiner

*Primary Examiner*—Todd E. Manahan
(74) *Attorney, Agent, or Firm*—Larson & Taylor, PLC

(57) ABSTRACT

The invention concerns dental implants, more particularly a dental implant (1) comprising an external thread (2) and an internal thread (6). Said dental implant (1) is made of zirconium oxide. The invention also concerns a method for moulding said dental implant using metal inserts (7, 9).

12 Claims, 5 Drawing Sheets

ZIRCONIUM OXIDE DENTAL IMPLANT WITH INTERNAL THREAD

Figure 1:
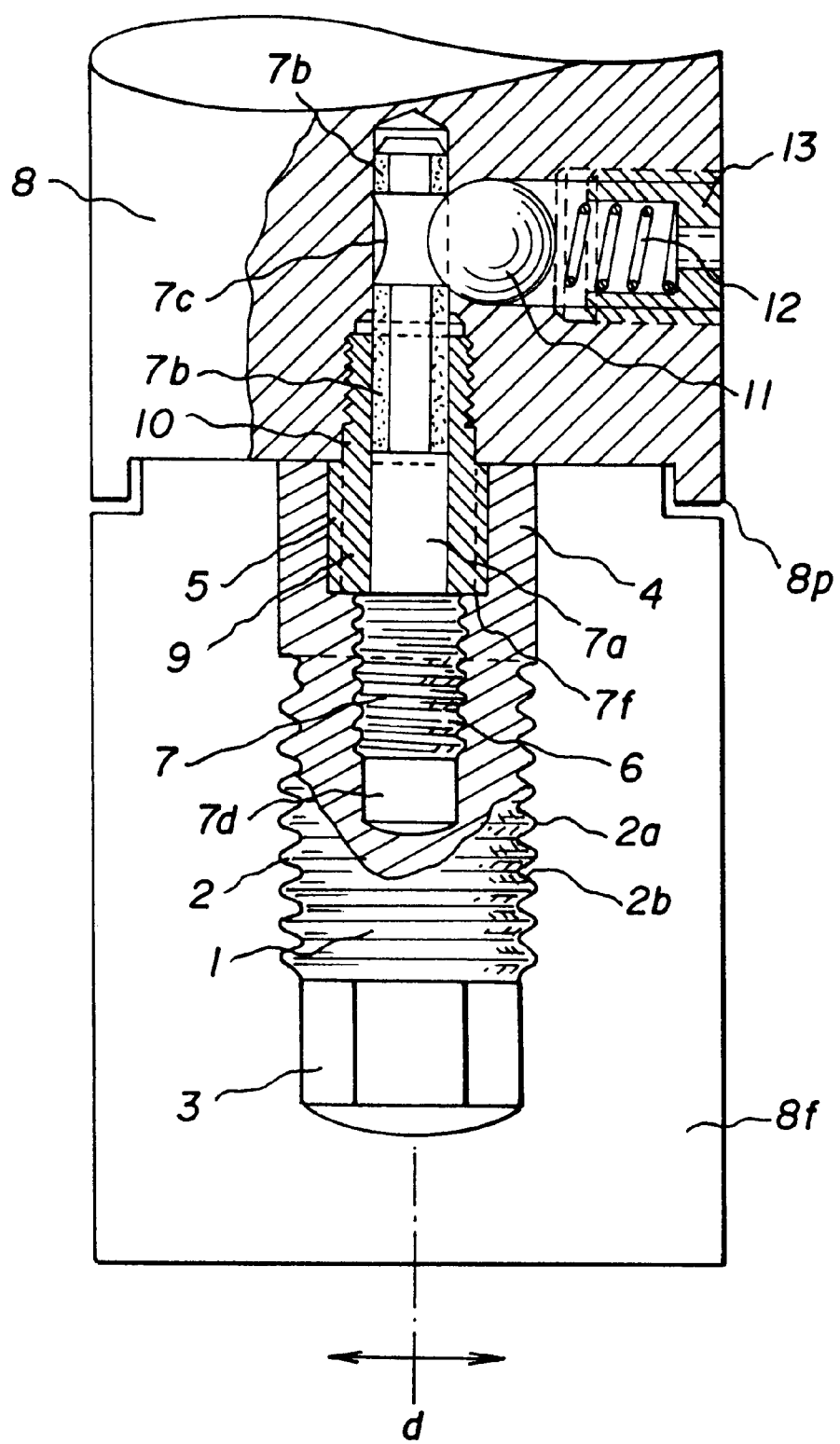
Figure 2:
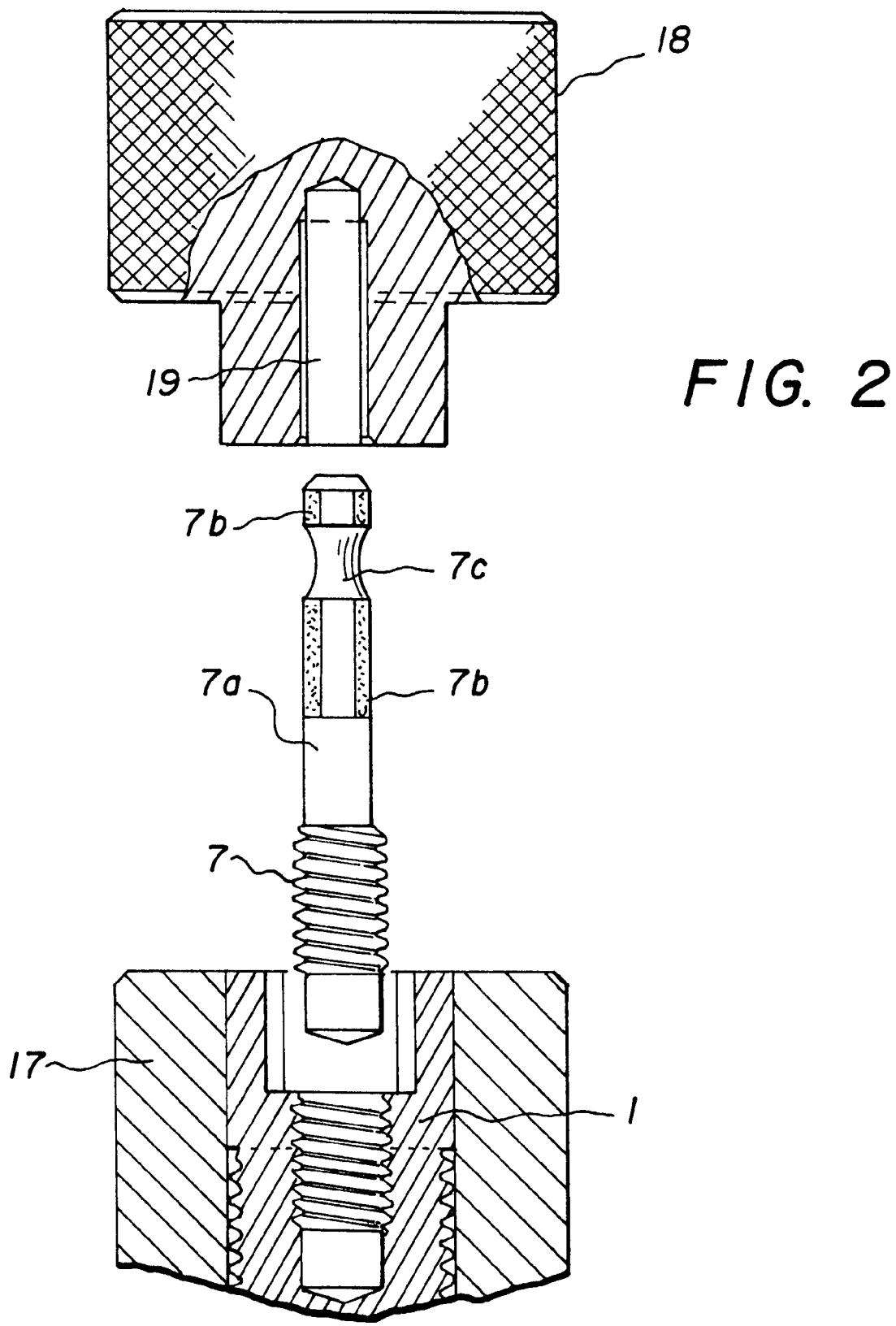
Figure 3:
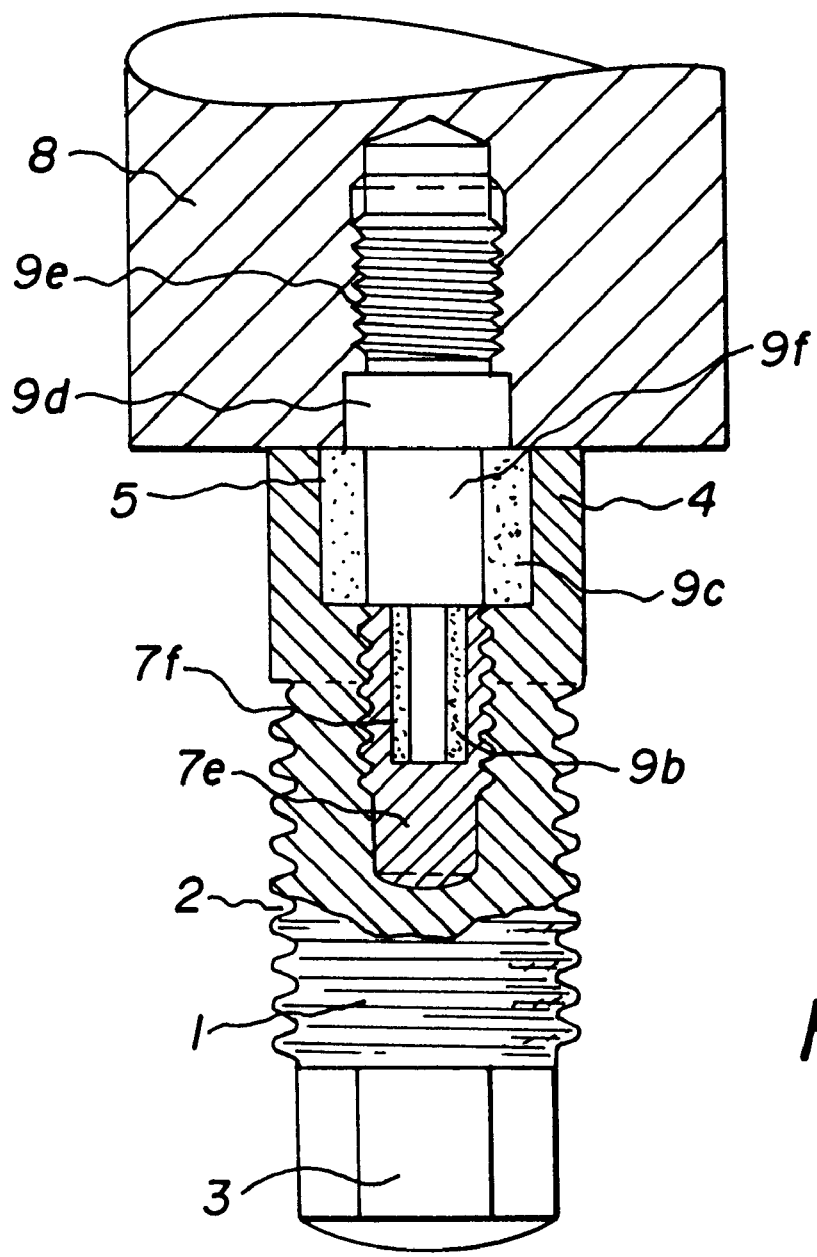
Figure 4:
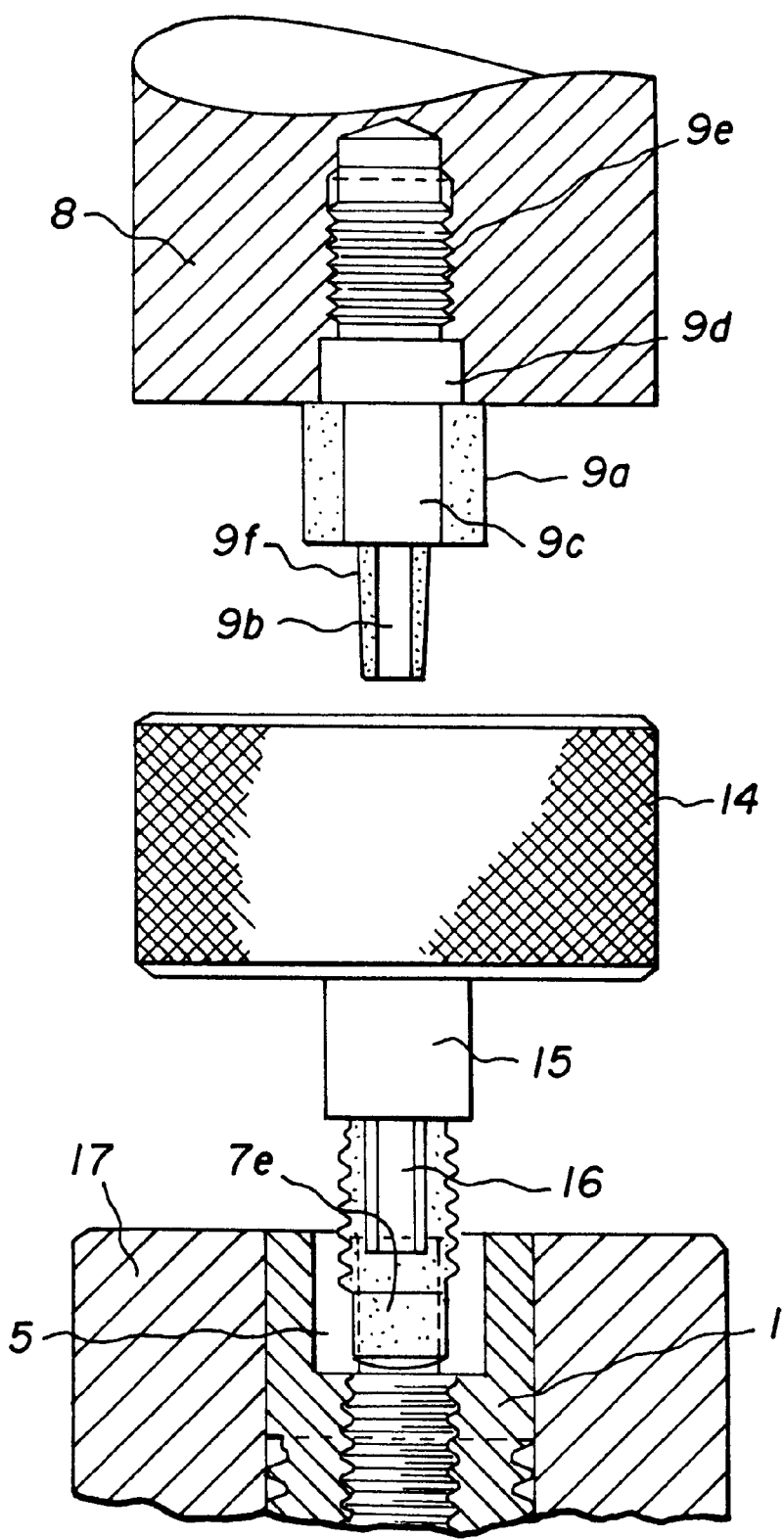
Figure 5:
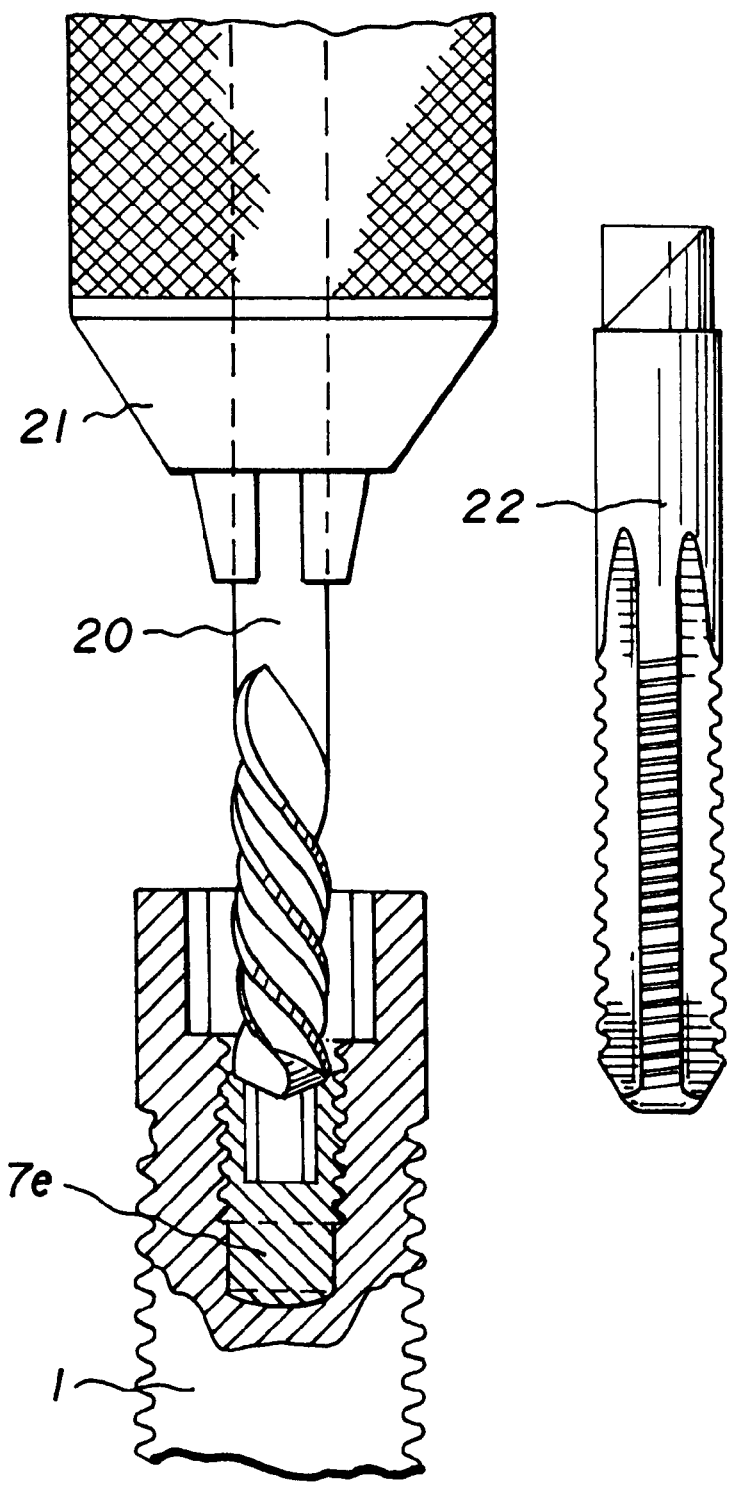

The present disclosure relates to dental implants, more particularly those with a central opening needed for setting up a threaded abutment or a parodontal ring.

These implants have to be installed in the human skeleton, preferably the dental skeleton and eventually the animal skeleton. In opposition to techniques using posts located in the natural root of the tooth, dental implants are set up after the extraction of the whole tooth. The osseous tissue after its rebuilding is then drilled for the fitting of the implant.

The majority of the implants valuable for osseous tissues is made of titanium as pure as possible. Titanium T 40, T50, T60 are mostly used. These titanium implants are generally tightly fitted in the bone drill hole, they can be coated with hydroxyapatite or porous titanium. An other possibility for these titanium implants is to be screwed in the bone, which gives a better security in the quality of the fixing.

Since a few years, new implants are under experimentation. Some of them have been adopted successfully like those made of zirconium oxide with a particularly good robustness linked to the hardness of the zirconium oxide material and consequently a longer life.

Zirconium oxide implants available today may have sometimes a central axial conical hole, the shape of which is polygonal, more often square or hexagonal. Their hole is obtained by moulding and then sintering and they can receive prosthetics with a similar shape which have to be adjusted in the well before fixing with a dental cement.

However, even with these techniques, the longevity of these zirconium oxide implants is not optimal. A possibility to improve the quality of these implants would be to give them a threaded central axial hole which would allow to fix an abutment within the implant with an appropriate screw.

In fact, due to the extreme hardness of the material, it is not possible to drill correctly this threaded hole once the implant has been molded.

The present invention gives in fact the solution to manufacture zirconium oxide based implants with a threaded central axial hole. This hole, following the invention, is made, during the molding of the implant with a wired insert which will reproduce within the implant the adequate tapping. This threaded insert is movable and can be put or changed on its support which is a mobile part of the mould. Threading is obtained by molding. One makes a sintering by injection in the mould under high pressure of a zirconium oxide paste which is then baked at high temperature. The threaded hole is used for reception of various prosthetics which are either directly screwed in the implant or eventually fixed with appropriate screws. These screws may become antirotational by application of a dental resinos cement.

Several solutions allowing the realization of the central threaded hole in the body of the implant will be proposed.

Threading is however always made during the molding of the implant by injection under high pressure of the zirconium oxide based material.

On the other hand, the implant itself is most frequently screwable. This means the present invention leads to the manufacture of a dental implant presenting a longer life then the presently existing implants.

One therefore speaks, following the invention, of a tap implant. This threading allows the set up of an adequate screw to fix the abutment over the implant.

The purpose of the invention is a zirconium oxide based dental implant with an external thread and characterized by a molded internal thread The invention proposes too the manufacturing process of such an implant.

The various aspects and advantages of the invention will appear more clearly in the description of the following drawings which are given only as indications and by no ways as limitations of the invention. These drawings do show:

Drawing 1 represents, according to the invention, a dental implant and its manufacturing tool allowing a first mode of realizing a central axial threaded hole in the zirconium oxide based dental implant Drawing 2 illustrates a method to remove the insert used for the manufacture of the implant described in the drawing 1

Drawing 3 represents a second mode of fabrication of a central axial threaded hole Drawing 4 is related to a method of extraction of the insert used for the manufacture of the implant presented on the drawing 3

Drawing 5 illustrates a method allowing the insert extraction in case of any difficulties encountered with the methods described on the drawings 2 and 4

According to the invention, drawing 1 does show a manufacturing process of zirconium oxide dental implant 1 offering a threaded central axial hole. The dental implant 1 presents an external thread 2 which can be triangular, symetric or asymetric but which comprises anyway summits 2a and rounded hollows 2b. A ploughed in extremity of this dental implant may eventually end with an hexagon 3. The upper end 4 of the implant 1 is cylindrical and polished along an height variable between 1 and 3 millimeters. This upper end 4 forms the neck of the implant. This neck 4 has a polygonal boaring, for instance hexagonal 5, extended towards the bottom of the implant by an internal thread 6.

This thread 6 is realized at the time of the molding with a first removable insert 7 which plays the role of the moulding insert. The tapping 6 has also summits and rounded hollows which generally ensure an higher stability of the threading.

According to the drawing 1 which represents the preferred method to realize the zirconium oxide based dental implant, the first threading insert 7 is used as reproductive organ in the dental implant 1 at the time of the molding. This first threaded insert 7 is fitted at its lower end with a small cylindrical part 7d corresponding to the diameter of the core of the internal tapping 6. The other end of the first threaded insert 7 emerges from the dental implant 1 and comprises, in the prolongation of the tapping 6, a smooth cylindrical part 7a followed by a polygonal, preferably hexagonal 7b part. This polygonal part is interrupted by a rounded bottom throat.

A mold allowing the realization of the dental implant 1 with its external threading 2 comprises among others a mobile part 8 and a mobile part 8f. In the mobile part 8 a second insert 9 also called auxiliary insert is adjustedly screwed.

The second insert 9 is provided with an hexagonal male part which fits exactly together with the boring 5 of the implant.1.and comprises a cylindrical smooth and hollow boaring 10a which allows to receive the first insert 7. The second insert 9 serves as guide of the first insert 7. He secures the precision of the positioning of the internal threading of the dental implant. The first insert 7 is thrust jammed in the second insert 9. The thrust exists at the level of a junction 7j between the tapping 6, the smooth cylindrical part 7a of the first insert 7 and the male hexagonal part 5 of the second insert 9. The combination of the mobile part 8 of the first insert 7 and of the second insert 9 makes a stamp which is affixed with centering on the fixed part 8*f* of the mold through a circular housing 8*p*. The upper polygonal end 10 of the second insert 9 is ploughed in the mobile part 8 of the mold in which one finds a ball 11 pushed by a spring 12. This spring 12 is leant against the ball 11 through an hollow screw 13 in contact with one end of the spring 12. This mechanism comprising the ball system 11, the spring 12 and the hollow screw 13 allows the insert 7 to be maintained within the mobile part 8 of the mold at the time of injection of the zirconium oxide based paste which will make the dental implant 1. The ball exerts a pressure on the rounded bottom throat and this holds back the insert 7 in the mobile part 8.

When the implant 1 is molded, the mobile part 8 associated with the insert 9 moves back but leave the insert 7 in position in the implant1. During this back motion, the ball 11 rolls progressively as it climbs over the hexagonal end 7*b* of the insert 7. The second insert 9 being slipped in the mobile part 8 of the mold moves back with this part 8.

The solution using the ball 11 is preferred to maintain the insert 7 during the injection of the implant. It could however be possible to maintain this insert 7 with a metallic rod going across the insert 7 through the mobile part 8. But a deterioration of the dental implant 1 would be probable if one would forget to pull out this rod when withdrawing the mobile part 8 whilst the ball system 11 doesn't necessitate any particular precautions during this withdrawal.

The fixed part 8 *f* of the mold is made by two pieces which can be separated according to an axis d centered over the mold and therefore can let the dental implant 1 become visible.

The drawing 2 illustrates a method allowing to pull out the insert 7 used in the manufacturing of the threaded dental implant presented on the drawing 1.

When the dental implant 1 still containing the insert 7 is pulled out of the mold, it is put into a square shaped metallic cage 17 and constricted in a vice in order to release the insert 7. The insert 7 is unscrewed with an hollow wrench 18 having a female polygonal, square or hexagonal form 19 fitting with the male polygonal, square or hexagonal form 7*b* of the insert 7. A knurled digital part 18 *a* facilitates the unscrewing of the insert 7. Although not represented on the drawing 2, the hexagonal shaped ploughed in end 3 mentioned in the description of the drawing 1 allows to bolt the implant during the unscrewing. On the other hand, it allows to make the dental implant 1 antirotational when it is implanted in the bone.

Drawing 3 represents an other method of manufacturing the dental implant 1. One can see several parts already presented in the description of the FIG. 1, the functions of which having been unchanged. This is the case for the dental implant 1, its external thread 2, its hexagonal end 3 and its neck 4. Neck 4 has always an hexagonal boring 5. In accordance with the method presented in the drawing 1, a first metallic insert 7*e* machined or sintered with summits and rounded hollows is used to reproduce the threading 2 of the dental implant 1. An hexagonal well 7*f* with parallel sides starting from the end of the threading is arranged in the first insert 7*e*. This well receives the hexagonal end 9*a* of a second insert 9*f* screwed in the mobile stamp 8 of the mold. Both inserts 7*e* and 9*f* are thus fitted together. The second insert 9*f* comprises an hexagonal end 9*b* which is slightly conical in order to tightly maintain the insert 7*e* at the end of the driving. Their horizontal position allows them to stay unmoved each with respect to the other. The second insert 9*f* is topped by an second hexagonal part 9*c* which serves as reproductive organ in the dental implant 1. A third smooth cylindrical part 9*d* follows after the hexagonal part 9*c*: it is used for the centering in the mobile part 8 of the mold. Finally, a last thread part 9*e* locks the second insert 9*f* in the mobile part 8.

Once the implant 1 is molded, the mobile stamp 8 moves back carrying the insert 9*f* screwed in it and leaving the insert 7*e* in the dental implant 1. As the 2 parts of the mold open, one has to recover the implant 1 after extraction of the insert 7*e*.

As indicated on the drawing 4, this extraction can be done with an ordinary unscrewing using a square metallic cage 17 tightened in a vice. After extraction of the mobile part 8 accompanied by the second insert 9*f*, it is enough to insert the implant 1 in this cage and to orient its hexagonal end 3 in the hexagonal female housing of the cage 17. One uses later on a digital wrench 14 comprising an hexagonal end 16 penetrating in the insert 7*e*. This wrench possesses a cylindrical diameter 15 which centers itself into the hexagon 5 of the implant 1. That is also a possible way to unscrew the insert 7*e*.

Drawing 5 presents an alternative in case of difficulties for unscrewing the insert 7*e*. One can pierce the insert 7 with a link twist-drill 20, a drilling machine the diameter of the drill being slightly lower than the core of the thread of the insert 7. Then one uses the control tap to pull out the small quantity of substance remaining in the threads of the insert.

Others techniques may also be used to facilitate the withdrawal of the insert 7 and 7*e*. One can for instance spray on the surface of the insert 7 or 7*e* a material which avoids the zirconium oxide based paste to stick on the metallic surface of the insert. One can also dip a few moment the molded implant 1 and the first insert 7 or 7*e* in liquid nitrogen at roughly −250° C. The first insert 7 or 7*e* and the implant 1 being of different nature, they will shrink differently: the first metallic insert 7 shrinks much more rapidly than the zirconium oxide based paste. The unscrewing of the first insert 7 is thus easier.

The above mentioned invention is presented under a preferential mode but not a limitative one. One can add to it a small compensating ring in order to raise the height of the implant of the thickness of the gum. This compensating ring called parodontal ring could be also based on zirconium oxide and threaded. Lastly, this type of threaded zirconium oxide based implant may find other applications outside the above mentioned dental scope. This type of implant may indeed be screwed in whatever part of the human skeleton and thus give rise to prosthetics.

What is claimed is:

1. A dental implant comprising:
   zirconium oxide having an external thread screwable in the osseous tissues; and
   an internal tapping obtained by molding.

2. The dental implant according to claim 1 further comprising summits and rounded hollows in both the external thread and the internal tapping.

3. The dental implant according to claim 2, further comprising smoothness over a height of a few millimeters of an upper end of the dental implant.

4. The dental implant according to claim 3 further comprising a hexagonal boring on an upper end of the dental implant.

5. The dental implant according to claim 2 further comprising a hexagonal boring on an upper end of the dental implant.

6. The dental implant according to claim 1, further comprising smoothness over a height of a few millimeters of an upper end of the dental implant.

7. The dental implant according to claim 6 further comprising a hexagonal boring on an upper end of the dental implant.

8. The dental implant according to claim 1 further comprising a hexagonal boring on an upper end of the dental implant.

9. A manufacturing process of a zirconium oxide dental implant provided with an external thread and an internal tapping comprising the steps of:

(a) screwing with centering of an auxiliary hollow insert in a mobile part of the mold of the dental implant thereby making a mobile stamp;

(b) fixing a molding insert used to reproduce the internal tapping imbedded in the mobile stamp through the auxiliary insert;

(c) affixing with centering of the mobile part associated with the molding insert on a mold determining the shape of the dental implant;

(d) sintering by injection in the mold under high pressure of a zirconium oxide based paste and its baking; and (e) withdrawing the mobile stamp leaving in situ the molding insert.

10. The manufacturing process according to claim 9 wherein the mobile stamp comprises a ball allowing to keep back the molding insert at the time of the injection of the paste.

11. The manufacturing process for a zirconium oxide dental implant according to claim 10, wherein one upper end of the auxiliary implant and one upper end of the molding insert entering in the auxiliary insert are polygonal.

12. The manufacturing process according to claim 10, wherein the molding insert comprises a lower cylindrical end with the same diameter than the core of the internal tapping.

* * * * *